United States Patent [19]

Coyle

[11] 4,103,176
[45] Jul. 25, 1978

[54] HAND-HELD COMPRESSOR FOR USE BY RADIOLOGIST

[76] Inventor: Maurice J. Coyle, 3326 Wesleyan Dr., Anchorage, Ak. 99504

[21] Appl. No.: 757,220

[22] Filed: Jan. 6, 1977

[51] Int. Cl.² ............................................. G21F 3/02
[52] U.S. Cl. .................................. 250/516; 250/519
[58] Field of Search ............................. 250/516, 519

[56] References Cited

U.S. PATENT DOCUMENTS

| 710,201 | 9/1902 | Lowder | 250/516 |
| 3,883,749 | 5/1975 | Whittaker et al. | 250/516 |

*Primary Examiner*—Harold A. Dixon
*Attorney, Agent, or Firm*—Graybeal, Barnard & Uhlir

[57] ABSTRACT

A hand-held radio-translucent compression device used by a radiologist for manipulating or depressing the abdomen to flatten portions of the intestinal tract which have been rendered radiopaque by a solution of barium sulfate or the like. The device is fabricated from a radiolucent material so that radiated signals through the patient's body will not be blocked by the radiopaque gloved hand of the radiologist. A relatively flat, planar body portion is formed to accommodate the user's gloved hand and is adapted to be gripped between the thumb and extended fingers. A rounded projecting portion is attached to the front of the body and includes a contact surface situated forwardly of the outstretched tips of the user's fingers. The sensitive fingertips of the user's hand, encased in a radiopaque glove for radiation shielding, can then be used to manipulate the abdomen and, in turn, explore the patient's lower digestive tract while observing the effects on the monitor of a fluoroscope. Optionally, a small opaque marker such as a so-called BB is impregnated in the plastic near the tip of the body.

7 Claims, 3 Drawing Figures

HAND-HELD COMPRESSOR FOR USE BY RADIOLOGIST

BACKGROUND OF THE INVENTION

1. Field of the Invention

This invention relates to a clinical aid for use in conjunction with fluoroscopes, and particularly, to a hand-held compression device for use by radiologists and other X-ray technicians to manipulate or depress portions of the patient's body without interfering or blocking the radiated signals of the fluoroscope through the area being evaluated.

2. Description of the Prior Art

Fluoroscopes have been used by radiologists and other doctors for many years to diagnose a multitude of ailments afflicting the human body. Such devices commonly project an X-ray flux through the body regions being evaluated and derive an image from the unabsorbed radiation on the monitor of a fluoroscope. As is known, prolonged exposure to such X-rays can have a harmful effect on the human body and the manifestation of repeated exposures is cumulative. While the composite effect would not reach a critical level for the patient who is only infrequently exposed to the radiated energy of X-rays, the diagnosing physician is repeatedly subject to such exposure. Since the body absorbs a portion of the flux of the X-rays, repeated exposures continually raise the composite dosage rate unless there is sufficient time between subsequent exposures to allow a natural decay of the dosage rate. For this reason, doctors who continually use X-ray devices such as fluoroscopes most often wear shielding garments such as aprons and gloves for decreasing their dosage rate by insulating themselves from exposure to the harmful radiation.

The protective value of such shielding garments results from a screening agent, often lead or uranium, which is disposed between the transmitter of the fluoroscope and the portion of the body sought to be protected. Since such devices absorb and block the X-rays in preventing the radiation from reaching the radiologists they are radiopaque and create a shadow on the monitor of a fluoroscope.

In one method of examining a patient for suspected digestive tract ailments, a solution of barium sulfate or the like is injested into the lower intestinal tract in order to detect the presence of tumors or polyps. As is known, such a solution is radiopaque as opposed to the human body which is, to a varying degree, radiolucent. The doctor then by manipulating and depressing the patient's abdomen over the intestinal tract can, in turn, flatten the digestive tract. With selected portions of the abdomen thus depressed, the doctor, while observing on the monitor of a fluoroscope, can identify tumors or polyps attached to the inner surface of the intestinal tract. However, as is apparent, the interpositioning of his hand enclosed in a radiopaque glove between the transmitter and receiver of the fluoroscope would create an opaque shadow on the monitor hindering diagnosis of the affliction.

Known prior art compressors which have been used by radiologists have included a spoon-shaped device, often formed from a radiolucent wood material. A long handle, attached at one end of a cup shaped body is gripped by the closed hand of the user. The doctor then uses the forward cup-shaped end to flatten the portion of the patient's body under analysis. A variation of this type of spoon shaped device, known as a Palparium Spoon and marketed by General Electric Company, is configured so the gloved index and middle fingers of the user are insertable between prongs at the sides of the device to aid in the holding of the same.

Other prior art devices have also included an inflatable balloon, likewise formed from a radiolucent material, and used to depress or manipulate the patient's body adjacent the area of interest. Such devices are particularly adapted to depress the abdomen of the patient who is lying on his stomach on the table of the fluoroscope.

Of particular interest with respect to shielding garments for use by doctors and particularly radiopaque gloves to prevent harmful X-ray radiation in a fluoroscopic zone from reaching the hand of the examining doctor are U.S. Pat. No. 3,883,749 to Whittaker et al and U.S. Pat. No. 2,328,105 to Strobino. Both patents disclose flexible gloves which are adapted to the needs of fluoroscope operators whose hands are frequently in the high energy field radiated by fluoroscopic devices.

Of general interest with respect to glove type devices attachable to a hand for a particular purpose is U.S. Pat. No. 3,672,351, granted to Ubersax et al and U.S. Pat. No. 3,903,544 to Rhee. The former describes a disposable glove for testing the contents of accessible body cavities, and the latter discusses a unitary flexible protective glove molded of a resilient material for use in the art of Karate.

SUMMARY OF THE INVENTION

According to one aspect of the invention, a hand-held compression device is provided which is particularly adapted to be used by radiologists or the like for manipulating and compressing the abdomen to, in turn, flatten the intestinal tract, rendered radiopaque by a solution of barium sulfate, in order that abnormal growths situated on the wall of the intestinal tract might be visible on a fluoroscope. A body portion of the compression device is sized and adapted to receive the user's hand thereon, palm open. The thumb and fingers squeeze a gripped portion of the body and allow the compression device to be maneuvered or guided by the doctor in his diagnosis. A rounded protrusion of relatively small area (e.g. less than two square inches) is attached to the front of the body portions and projects forwardly therefrom beyond the extended fingers of the user's hand. A contact surface is provided at the front of the rounded protrusion on the underside thereof.

According to another aspect of the invention, the hand-held compression device according to the invention is provided with a flat relatively planar body portion which is held between the outstretched fingers and thumb of the user's hand. One face of the body is contoured to receive the fingers of the user's hand in adjacent valleys extending lengthwise thereon. The face situated on the opposite side of the body portion also includes a lengthwise extending valley which is adapted to receive the user's thumb.

According to still another aspect of the invention, a hand-held compression device for use by radiologists or the like to manipulate and depress a portion of the body during fluoroscopic analysis is provided with a plurality of laterally adjacent finger receiving valleys thereon. The sensitive fingertips of the user's hand can then be used to manipulate the outward end of the compression device in contact with the with the user's body, with the hand in much the same attitude as it would be if the device were not used.

According to still another aspect of the invention, a hand-held compression device is provided with a rounded protrusion which extends forwardly of the user's outstretched fingers and is particularly adapted to manipulate the portion of the body under fluoroscopic examinations. A radiopaque marker is situated in the forward end of the rounded protrusion adjacent the contact surface so that the position of the contact surface can be observed on the monitor of the fluoroscope.

According to yet another aspect of the invention, a hand-held compression device for use in fluoroscopic analysis is provided which can be fabricated at a low cost from a radiolucent material such as polyurethane or the like. The body portion of the compression is particularly adapted to be contoured to the user's hand for maximum control and sensitivity.

DESCRIPTION OF THE PREFERRED EMBODIMENTS

Figure 1:
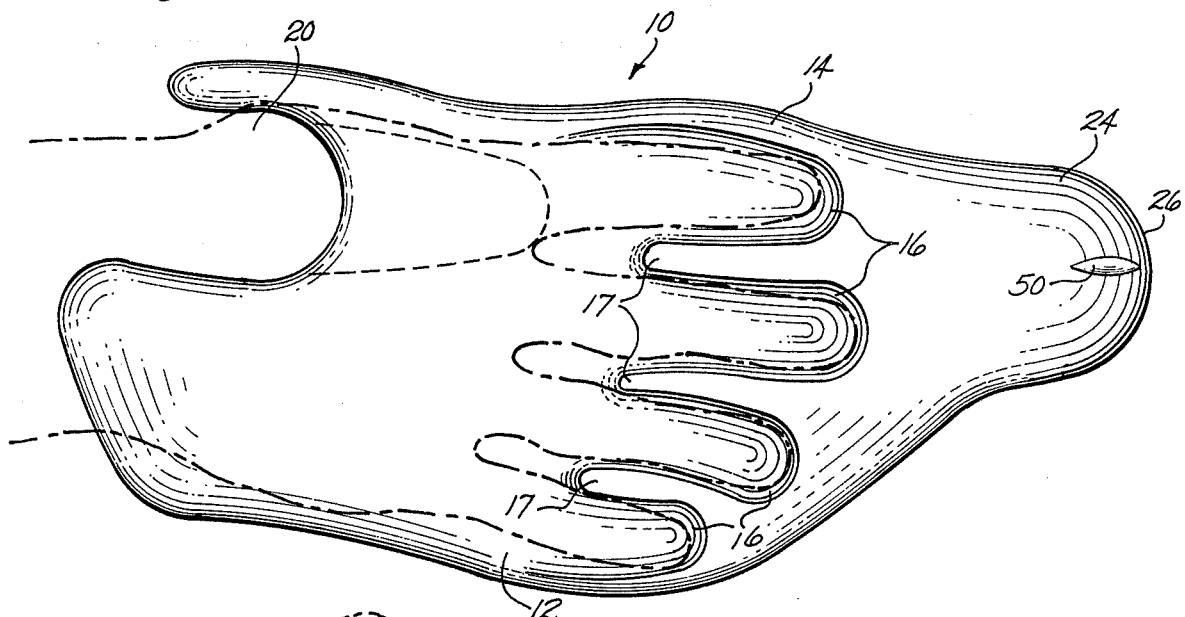
FIG. 1 is a top view of a first embodiment of a hand-held compressor according to the instant invention and illustrates a user's hand gripping the finger receiving face.
Figure 2:
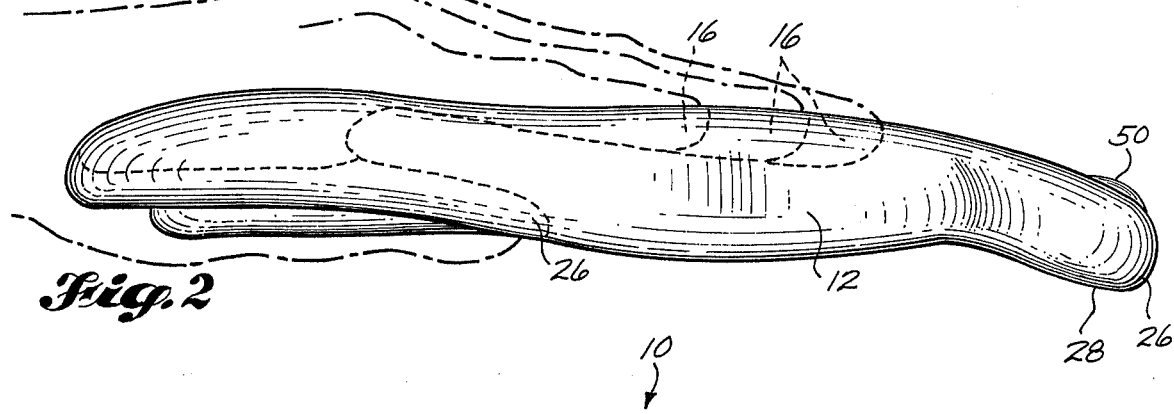
FIG. 2 is a side elevational view of the embodiment illustrated in FIG. 1.
Figure 3:
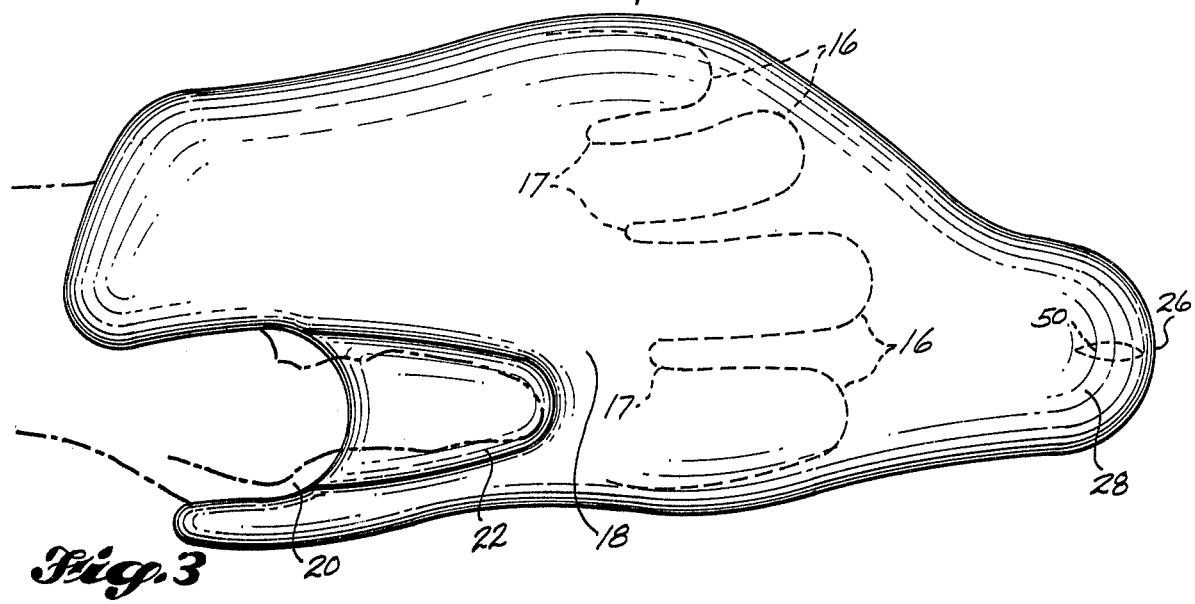
FIG. 3 is a bottom view of the embodiment illustrated in FIG. 1, but depicting the opposite or thumb receiving face.

FIGS. 1 - 3 illustrate a typical form of my hand-held compression device 10 for use by a radiologist. Compression device 10 comprises a body 12 especially adapted to accommodate the user's hand thereon. Body portion 12 is configured to have a width at least equivalent to the palm portion of the user's hand so that the compression device can be comfortably gripped between the outstretched thumb and fingers with the palm of the hand open.

A finger receiving face 14 (FIG. 1) is formed on the top of body 12 and is particularly contoured to receive the outstretched fingers of the user's gloved hand. A plurality of finger receiving valleys 16 are formed on face 14 and are sized to loosely receive the outstretched fingers of the user's hand. Each valley 16 cradles or cups the forward portion of each of the user's outstretched fingers in order that the compression device 10 can be manipulated by the fingertips of the user's hand. Adjacent finger valleys 16 are separated by a narrow lengthwise extending ridge 17.

As best seen in FIGS. 2 and 3, on the bottom of body 12 a thumb receiving face 18 is provided and is molded to accomodate the thumb of the user's hand. A rear opening notch 20 is provided at the back of body portion 12 and is displaced laterally to one side thereof. Preferably, notch 20 is approximately aligned on body 12 with the finger valley 16 which accommodates the user's index finger. A thumb valley 22 is formed on face 18 and is particularly adapted to receive the thumb of the user's hand therein. Thumb valley 22 also cradles or partially cups the lower portion of the user's thumb. Thumb valley 16, situated on face 18, and on the opposite face of finger valley 16 which receives the user's index finger, are approximately aligned in order that compression device 10 can be comfortably squeezed between the user's thumb and index fingers.

Projecting portion 24 is formed on the front of body 12 forwardly of finger valleys 16. In preferred form, said projection 14 is rounded or curved at its distal end so that there are no sharp corners which will cause discomfort when manipulating the area of the patient's body under fluoroscopic analysis. As is best seen in FIG. 2, the outward or distal end of projection 24 is also tapered so that tip 26, disposed at the outward end thereof, has a decreasing stiffness gradient. This causes tip 26 to be more pliable or bendable than body 12 so that it will give when it contacts the patient's body.

A contact surface 28 is formed on the underside of projection 24 near distal end 26. Projection 24 is shaped so that contact area 28 is approximately the same combined area as the index and middle finger of the user's hand. Since these are the two fingers most often used by diagnosing physicians, they also would be the fingers which would most likely have developed the greatest sensitivity and the most advanced dexterity.

Hand-held compression device 10 is particularly sized and shaped to conform to the user's hand in order that it might act as an extension of the fingers thereof, and particularly the index and middle fingers. As heretofore indicated, most diagnosticians prefer to use their index and middle fingers for probing the patient's body because of their high degree of dexterity and sensitivity. Projection 24 protrudes forwardly and downwardly from body 12 in much the same manner as the slightly curved fingers of the hand. In addition, the shape of contact surface 28, formed on the lower side of projection 24, is somewhat rounded in much the same manner as the tips of the index and middle fingers. This resemblance to the hand enhances the ability of the doctor to use his already developed sense of touch without interfering with the fluoroscopic picture on the monitor.

It has been found that it is often helpful for the physician to be able to identify the precise positioning of the probe on the fluoroscope monitor as he manipulates the patient's body. Referring again to FIGS. 1 - 3, first embodiment 30 of the hand-held compression device is preferably provided with a marker 50 which is visible on the monitor of a fluoroscope. In preferred form, projection 24 is disposed in the forward end of body 12 near the distal end 26 of projection 24. Marker 50 is situated on finger receiving face 14 and is approximately mid-way between either side of projection 24. Alternatively, the marker can simply be a so-called BB impregnated in the forward end of the body 12.

The use of a hand-held compression device according to the invention as a clinical aid by a physician in diagnosing certain ailments will be described. A known diagnostic technique involves the use of a fluoroscope to detect the presence of tumors or polyps in the lower digestive tract. A solution of barium sulfate or like radiopaque solution is first injected into the patient's lower digestive tract. The patient is then positioned between the transmitter and receiver of a fluoroscope in order that the diagnosing physician might observe the intestinal tract on the fluoroscope monitor. The portion of the X-ray flux which is unabsorbed or blocked by the patient's body is utilized by the fluoroscope to derive a visual presentation on the monitor.

As heretofore described, since exposure to the flux energy of the fluoroscope is cumulative, the hands and body of the diagnosing physician are normally garbed in a radiopaque shield to reduce his dosage rate of harmful X-rays. If the radiopaque gloved hand of the physician were interposed in the radiated energy path, this interlination would be manifest on the fluoroscope monitor as a blackened area. However, in that tumors or polyps are sometimes only visible on the monitor of a fluoroscope when the patient's abdomen is depressed or manipulated, the hand-held compression device according to the instant invention is particularly well-suited as a depressor since it acts as an extension of the user's hand.

As the patient's abdomen is explored with the contact area of the compression device, the presence of tumors or polyps in the lower digestive tract can be observed on the fluoroscope monitor as lightened points in an area darkened by the barium sulfate. In addition, the precise positioning of the probe end of the compression device, normally invisible on the fluoroscope monitor due to its fabrication from a radiolucent material, can be readily observed by the marker which also appears in darkened form on the fluoroscope monitor. By utilizing a hand-held compression device according to the instant invention, the diagnosing physician's ability to correlate the precise area being probed by the compression device with the picture presented on the monitor of the fluoroscope is enhanced.

In preferred form, the hand-held depressor of the instant invention is fabricated from a relatively radiolucent material such as polyurethane except for the radiopaque marker. Such a material is relatively light in weight yet is sufficiently strong and durable for extended use as a clinical aid. Of course, such material really transmits energy in the form of radiated X-rays therethrough and would be relatively invisible on the monitor of a fluoroscope.

The embodiment shown in FIGS. 1 - 3 is typically approximately 10 inches in length and 5 ½ inches in width at its widest point which is about mid-way between distal end 26 and the rear portion thereof. At the forward end of body 12, projection 24 has a nominal width of approximatley 1 ½ inches which approximately corresponds to the combined width of the index finger and first finger. Notch 20, also rounded at its forward end, also has a nominal width of approximately 1 ½ inches.

From the foregoing, various modifications, revisions and adaptations of the hand-held compression devices according to the instant invention will occur to those skilled in the art to which the invention is addressed, within the scope of the following claims.

What Is claimed Is:

1. A hand-held compression device for use by radiologists or the like for manipulating or compressing the abdomen to flatten selected portions of the intestinal tract of a patient into whom radiopaque solution of barium sulfate or the equivalent has been injested in order that abnormalities situated in the intestinal tract such as tumors or polyps are visible on a fluoroscope, said compression device comprising:

a relatively strong and broad body portion having first and second opposed, generally parallel faces and being sized to have a width at least equivalent to the palm portion of the user's hand and contoured on at least one face to accommodate the user's fingers thereon and be gripped between the thumb and fingers of the hand with the hand palm open, a relatively strong and small rounded protrusion projecting forwardly from the front of said body portion and of a width less than said body portion, said protrusion coacting with said body portion during use and including a generally rounded contact portion situated at the end of said protrusion, and adapted to be used to manipulate the patient's abdomen when the user's hand is gripping said body portion, and wherein at least said contact portion is formed of a radiolucent material so that when the user's hand gripping said body portion is fully enclosed in a radiopaque covering, such as a glove or the like, the contact portion situated forwardly of the user's hand can be used to manipulate and depress the patient's abdomen without blocking or otherwise interfering with the radiated signals of the fluoroscope through the area being evaluated, and wherein said contact portion has a contact surface and said contact surface and one of said first and second faces are on the same side of said compression device and lie generally in the same plane whereby the protrusion being of small area is generally more pliable than the main body and acts as an extension of the fingers of the user.

2. A hand-held compression device according to claim 1, wherein the body portion of the compression device is a generally flat planar member wherein said first face includes a contoured portion to receive the outstretched fingers of the user's hand, and said second face includes a contoured portion to receive the user's thumb, so that said body portion can be securely gripped between and manipulated by the outstretched fingers and thumb of the user's hand.

3. A hand-held compression device according to claim 2, wherein said contoured portion of said first face on said compression device further includes a plurality of finger valleys thereon, each adapted to receive one of the user's fingers therein when said body portion is gripped by the user's hand, and wherein each valley is separated from the adjacent valley by a ridge.

4. A hand-held compression device according to claim 2, wherein said contoured portion of said second face further includes a valley adapted to receive the user's thumb when said body portion is gripped by the user's hand.

5. A hand-held compression device according to claim 1, wherein said protrusion projecting from the front portion of said body tapers toward said contact portion and has a decreasing stiffness gradient near said contact portion.

6. A compression device according to claim 1, wherein said protrusion which projects from the front of said body portion further includes a marker situated adjacent the contact portion, said marker being radiopaque so that the relative positioning of the marker can be identified on said fluoroscope.

7. A hand-held compression device according to claim 1, wherein the compression device is formed of polyurethane.

* * * * *